United States Patent
Hack et al.

(10) Patent No.: US 11,014,283 B2
(45) Date of Patent: May 25, 2021

(54) METHOD FOR STERILIZING A BLOW MOLDING MACHINE, AND BLOW MOLDING MACHINE

(71) Applicant: KRONES AG, Neutraubling (DE)

(72) Inventors: Andreas Hack, Dingolfing (DE);
Florian Geltinger, Donaustauf (DE);
Jochen Hirdina, Regensburg (DE)

(73) Assignee: KRONES AG, Neutraubling (DE)

( * ) Notice: Subject to any disclaimer, the term of this patent is extended or adjusted under 35 U.S.C. 154(b) by 0 days.

(21) Appl. No.: 16/609,455

(22) PCT Filed: May 11, 2018

(86) PCT No.: PCT/EP2018/062189
§ 371 (c)(1),
(2) Date: Oct. 30, 2019

(87) PCT Pub. No.: WO2018/206753
PCT Pub. Date: Nov. 15, 2018

(65) Prior Publication Data
US 2020/0061899 A1 Feb. 27, 2020

(30) Foreign Application Priority Data
May 11, 2017 (DE) ...................... 10 2017 110 272.8

(51) Int. Cl.
*B29C 49/46* (2006.01)
*B29C 49/48* (2006.01)
(Continued)

(52) U.S. Cl.
CPC ................ *B29C 49/48* (2013.01); *A61L 2/10* (2013.01); *A61L 2/18* (2013.01); *A61L 2/186* (2013.01);
(Continued)

(58) Field of Classification Search
CPC . B29C 49/46; B29C 49/48; B29C 2049/4858; B29C 2049/4697
See application file for complete search history.

(56) References Cited

U.S. PATENT DOCUMENTS

| 10,000,027 B2 | 6/2018 | Voth et al. |
| 2009/0178264 A1 | 7/2009 | Stoiber |

(Continued)

FOREIGN PATENT DOCUMENTS

| EP | 2080606 A2 | 7/2009 | |
| EP | 2468478 B1 * | 2/2013 | ............. B29C 49/46 |

(Continued)

OTHER PUBLICATIONS

International Search Report dated Aug. 29, 2018 for PCT/EP2018/062189.

*Primary Examiner* — Robert B Davis
(74) *Attorney, Agent, or Firm* — Schmeiser, Olsen & Watts, LLP

(57) ABSTRACT

Provided is a method for operating a device for shaping plastic preforms to form plastic containers, wherein the device has a movable support on which a plurality of shaping stations for shaping plastic preforms to form plastic containers are arranged, and these shaping stations each have blow molds that are suitable for and intended for molding the plastic preforms and are arranged at least indirectly on blow mold supports. The blow molds are kept at least temporarily in a magazine device, wherein this magazine device is suitable for and intended for receiving several sets of blow molds.

18 Claims, 1 Drawing Sheet

Figure 1:
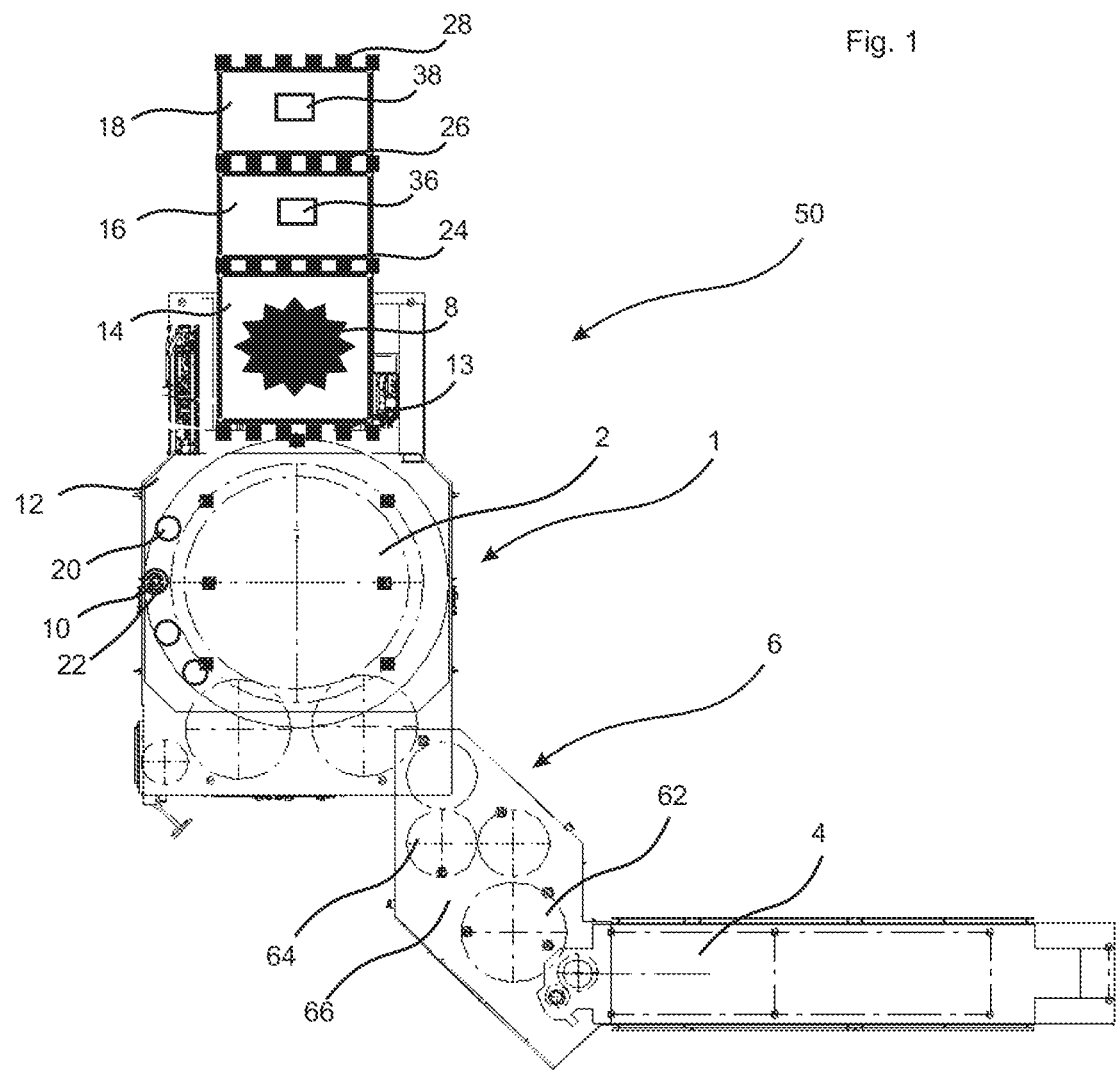

(51) Int. Cl.
    *A61L 2/10*    (2006.01)
    *A61L 2/18*    (2006.01)
    *A61L 2/26*    (2006.01)
    *B29C 49/78*   (2006.01)
    *B29L 31/00*   (2006.01)

(52) U.S. Cl.
    CPC ............... *A61L 2/26* (2013.01); *B29C 49/46* (2013.01); *B29C 49/78* (2013.01); *A61L 2202/18* (2013.01); *A61L 2202/23* (2013.01); *B29C 2049/4697* (2013.01); *B29C 2049/4858* (2013.01); *B29C 2949/78563* (2013.01); *B29C 2949/78848* (2013.01); *B29L 2031/712* (2013.01)

(56) References Cited

U.S. PATENT DOCUMENTS

| | | | |
|---|---|---|---|
| 2011/0061690 A1* | 3/2011 | Seger | B29C 49/42 134/137 |
| 2015/0145178 A1 | 5/2015 | Blochmann | |
| 2015/0145179 A1 | 5/2015 | Finger et al. | |
| 2015/0151455 A1* | 6/2015 | Cirette | B29C 49/28 425/526 |
| 2015/0306828 A1 | 10/2015 | Geltinger et al. | |
| 2019/0009449 A1 | 1/2019 | Kindl et al. | |

FOREIGN PATENT DOCUMENTS

| | | |
|---|---|---|
| EP | 2878424 A1 | 6/2015 |
| EP | 2878425 A1 | 6/2015 |
| EP | 2918391 A1 | 9/2015 |
| EP | 2937203 A1 | 10/2015 |
| WO | 2017103281 A1 | 6/2017 |

\* cited by examiner

METHOD FOR STERILIZING A BLOW MOLDING MACHINE, AND BLOW MOLDING MACHINE

CROSS-REFERENCE TO RELATED APPLICATIONS

This application claims priority to PCT Application No. PCT/EP2018/062189, having a filing date of May 11, 2018, based on German Application No. 10 2017 110 272.8, having a filing date of May 11, 2017, the entire contents both of which are hereby incorporated by reference.

FIELD OF TECHNOLOGY

The following relates to a method for operating a reshaping device for reshaping plastic parisons into plastic containers and in particular to a method for sterilising such plants and/or for mounting and demounting blow molds. In addition, the following relates to a machine for reshaping plastic parisons into plastic containers.

BACKGROUND

It has been known for a long time from the known art that plastic parisons are heated in an oven and in this heated state are blow molded to produce a plastic bottle. For this purpose, the heated plastic parisons are introduced into blow molds and inside these blow molds are acted upon by compressed air. If different containers are to be blow molded, the blow molds must be changed. For this purpose, it is known from the known art that the parts of the blow mold, such as in particular the side parts and base parts thereof, are released from the supports and are replaced by other blow molds.

In addition, more recently, sterile blow molding machines have become known from the known art. Such blow molding machines can be used for example in order to produce plastic containers which are already sterilized and which are required in particular for filling with sensitive beverages. In this case it is necessary also to sterilise the respective machine at predetermined time intervals In such a sterile or aseptic blow molding machine a change of blow mold is carried out in a specially isolated area by an operator in the current internal known art in the name of the applicant. A machine which actuates the mold support enables the operator to remove the blow molds from the mold support via a window to the sterile region of the blow molding wheel. In this case the blow molds are stored, separated into base mold and two side parts or mold shells, in a special blow mold magazine, which is accommodated in a special isolation region. After the manual change of the blow molds the sterile region of the blow molding wheel with the inserted molds is sterilized, for example by means of hydrogen peroxide or $H_2O_2$.

Therefore, in the known art sterilising of the blow molds takes place only if they are inserted into the mold support. Therefore, in the known art it is not possible to completely sterilise the spaces at the rear of the blow mold (both of the base mold and also the mold shells) and the corresponding counterpart faces in the mold support.

In addition, dirt and other particles can enter the otherwise hermetically separated sterile region through the operator and an interface to the mold change. Furthermore, a manual change of the blow molds, separated into base mold and two side molds, causes long setup times and thus high setup costs.

SUMMARY

One aspect of the embodiments of the invention is based is to reduce the setup times for such installations. In addition, a possibility should be created for achieving a more complete sterilization of the installations.

Often in addition to or instead of the sterilization a change of blow mold is also necessary, in particular in order to enable a changeover to the production of other beverage containers. In the case of a manual change of the blow molds, the blow molds are usually stored in a mold wagon. In the case of an automatic mold change, which has become known more recently from the internal known art of the applicant, a robot is used, and mold storage takes place in a blow mold magazine and also, in the case of an aseptic blow molding machine, in a correspondingly aseptic blow mold magazine. In this case it is known that, except by the automatic mold change by means of a robot, the blow molds separated into base mold and two side parts are individually placed in and stored in a mold store.

Since each blow mold set is separately stored, separated into base mold and two side parts, in a mold wagon or a blow mold magazine, and the mold wagon or the blow mold magazine is stored outside the machine, storage costs ensue and in addition a change of blow mold requires a long preparation time (caused for example by the transport of the mold wagon or of the blow mold magazine from a store, the changing of the blow mold magazine in the case of automatic mold change and for example an additional test run of the robot), which is necessary because checks should be performed as to whether the correct molds are present and are correctly inserted.

In addition, when the blow molds are stored outside a machine there is a danger, in particular during transport, of damage or ingress of dirt.

Therefore, a further aspect of the embodiments of the invention is to make such a blow mold change simpler or easier. These aspects are achieved according to the embodiments of the invention by the subjects of the independent claims. Advantageous embodiments and modifications are the subject matter of the subordinate claims.

In a method according to the embodiments of the invention for sterilising a machine for reshaping plastic parisons into plastic containers the machine has a movable and in particular rotatable support, on which a plurality of reshaping stations for reshaping plastic parisons into plastic containers are arranged. In this case these reshaping stations each have blow molds which are suitable and intended for shaping the plastic parisons, and which are arranged at least indirectly on blow mold supports. According to the embodiments of the invention the blow molds are removed from the blow mold supports at least temporarily before and/or during the sterilization of the machine and/or before and/or during sterilization of the blow molds.

Thus within the context of the embodiments of the invention it is proposed that the blow molds are removed from their supports in order also to achieve complete sterilization in particular also of the rear regions of the blow molds and the corresponding portions of the mold supports on which these rear portions are arranged.

Furthermore, the embodiments of the present invention is directed to a method for operating a machine for reshaping plastic parisons into plastic containers and in particular to a method for mounting and demounting blow molds on such machines. In this case the machine has a movable and in particular rotatable support, on which a plurality of reshaping stations for reshaping plastic parisons into plastic containers are arranged. In this case these reshaping stations each have blow molds which are suitable and intended for shaping the plastic parisons, and which are arranged at least indirectly on blow mold supports.

According to the embodiments of the invention these blow molds are at least temporarily stored in a magazine device, wherein this magazine device is suitable and intended for accommodating a plurality of sets of blow molds.

Thus, in this configuration according to the embodiments of the invention, which can also be used independently of the configurations described above, the provision of a magazine device is proposed, which can accommodate a plurality of sets of blow molds. In this way a change of blow mold can be carried out in a simplified manner. In this case, as mentioned above, the magazine device can also be arranged in a clean room, and can also have the characteristics already described above.

In general, it is also possible that one or more magazine devices are provided, but only one blow mold set is stored per magazine device. Thus, a store and/or a sterile room can be provided, wherein a plurality of magazine devices which each serve to accommodate (precisely) one blow mold set can be provided in this sterile room. A store as described above which is suitable and intended for accommodating a plurality of blow molds is also designated below as a dynamic store.

In this case the embodiments of the invention is directed to a method for modifying machines and in particular for changing blow molds on machines. It is pointed out that, in the manner described, other components of a reshaping station can also be changed, such as for example stretching rods, blow molding dies, and the like.

The applicant reserves the right also to claim protection for a corresponding method for modifying other change parts.

The blow molds are removed and/or installed again by means of a changing robot. In a further advantageous method, the respective blow mold set is selected by means of a robot. In this case it is possible that the robot identifies the blow mold set by means of an identification device. However, it would also be possible that the respective blow mold set is selected by means of a control device and in particular by an operator by means of a control device.

In a further preferred method, the blow molds removed from the supports are stored at least temporarily in a magazine device. In a further preferred method this magazine device is also sterilized at least temporarily. The blow molds are also sterilized at least temporarily.

In a further preferred method, the blow molds are removed in sterilized form from the magazine device. In a further preferred method the blow molds removed from the magazine device are also sterilized, wherein this sterilization can also take place before and/or during the storage in the magazine device. In this case too, the sterilization can take place by application of a sterilising agent. Furthermore, it is also possible that the blow molds are sterilized during their storage in the magazine. In addition, the magazine device itself can also be sterilized.

At least one sterilization takes place inside a clean room, in which a plurality of reshaping stations for reshaping plastic parisons into plastic containers is transported in an operating mode.

In this case these reshaping stations each have blow molds which are suitable and intended for shaping the plastic parisons, and which are arranged at least indirectly on the blow mold supports.

In a preferred method at least several of the blow molds and all of the blow molds are removed from the blow molds before the machine or regions of the machine are sterilized.

In a further preferred method, the blow molds are changed by means of an automatic changing device and in particular by means of a changing robot.

Accordingly, instead of the manual change of blow mold by an operator, in this method a robot is used which changes the blow molds fully automatically. In this case it is conceivable that the robot is suitable for a clean room or sterile room, and/or is designed to be sterilisable for example by a sterilising agent such as H2O2 and/or is separated (in particular hermetically) from a sterile room of the machine by a protective cover which is suitable for a clean room or sterile room and is particularly sterilisable by a sterilising agent such as H2O2. Lines such as for example cables and/or pneumatic lines and/or hydraulic lines of the changing robot run, inside the changing robot or also inside a protective cover, in a predetermined region, for example downwards.

Thus, the changing robot is designed to be sterilisable and/or is located in a sterile room.

In a particularly preferred embodiment this robot is arranged on a rear side of the machine, for example a side opposite the side on which pitch alteration starwheels are located.

The robot is located in a robot cell and in particular a sterilisable robot cell. In this case this robot can form an extended sterile room with the changing robot. In addition, this extended sterile room with the changing robot can be adjoined by a second extended sterile room in which for example one or more blow mold magazines can be provided to accommodate the blow molds.

This mold magazine is designed in such a way that the blow molds can be accommodated therein so as to be sterilisable and in this case can be particularly held spaced apart. This blow mold magazine itself is sterilisable and the blow molds arranged in the blow mold magazine are also sterilisable and in particular sterilisable inside a sterile room. Thus it would be possible for example that mold shells and/or side parts of the blow molds on the one hand and base parts of the blow molds on the other hand are held spaced apart in order to be able to sterilise the mold shells and/or side parts all over.

In this case it is possible that the blow mold magazines are introduced by means of an access such as for example by means of a bulkhead which particularly seals off an extended sterile room (hermetically) from the surroundings.

In addition, it is also possible that two sterile rooms are provided, which are, however, regarded as one sterile room and in which a mold change robot and one or more blow mold magazines are accommodated. In this case for example the sterile room with the mold change robot can be separated hermetically from a sterile room of the blow molding wheel (or the reshaping stations) by means of a first bulkhead. In addition, it would also be possible that two sterile rooms are regarded as one sterile room and are separated hermetically from the sterile room of the blow molding wheel by means of a bulkhead.

If a bulkhead is present, a change of blow mold can be prepared for example during the production, since the mold change robot and regions lying behind it are separated hermetically from the sterile room of the blow molding wheel by means of the bulkhead. In addition, it would also be possible that a sterile room is separated, in particular hermetically, by means of a second bulkhead from another sterile room. In this case it is possible that this first sterile room is connected to the sterile room of the blow molding wheel, and in this way blow mold magazines can be changed during production.

In addition, bulkheads can also be provided which separate the sterile room of the blow molding wheel hermetically from the environment and/or further sterile rooms. In addition it would also be possible that a sterile room for the blow mold magazine and a sterile room for the mold change robot are regarded as one sterile room and are connected with a sterile room of the blow molding wheel without needing a bulkhead. In addition, however, particularly these two sterile rooms would also be separated, in particular hermetically, from the environment by means of a further bulkhead. However, in this procedure a preparation for changing blow molds during the production is not possible.

In a preferred method a sterilization of the machine takes place by application of a flowable sterilising medium at least to components of the machine. Particularly this sterilising medium is a sterilizing medium such as in particular but not exclusively H2O2 or peracetic acid.

In addition, however, it would also be possible that a sterilization takes place by irradiation of plant parts for example with electromagnetic radiation and/or with UV light or the like.

In a further preferred method, after sterilization has taken place the blow molds are arranged on the blow mold supports again. In this case it is possible that the same blow molds which were already used previously, are again arranged, or also that new blow molds are fastened to the blow mold supports. A sterilization of the blow mold supports takes place after demounting of the individual reshaping stations.

In a further preferred method, the blow molds removed from the support are stored at least temporarily in a magazine device. In this case it is conceivable that this magazine device is also sterilized temporarily. In addition, it is also possible that in a preferred method the blow molds stored in the magazine device are sterilized. This sterilization also takes place by application of a flowable sterilising medium to the corresponding molds or regions of the magazine.

In a further preferred method, after sterilization has taken place, a new set of blow molds is arranged on the blow mold supports. Thus, in this method, in addition to the sterilization of the blow molds a change of blow mold can also be carried out.

In a further preferred method, the removed blow molds are also sterilized. In this case a sterilization of the blow molds is also possible during the storage thereof in the magazine.

Furthermore, the present embodiments of the invention are directed to an arrangement for reshaping plastic parisons into plastic containers. This arrangement has a movable support on which a plurality of reshaping stations for reshaping plastic parisons into plastic containers are arranged, wherein these reshaping stations each have blow molds which are suitable and intended for shaping the plastic parisons, and which are arranged at least indirectly on the blow mold supports. Furthermore, the machine has a clean room which at least partially surrounds a transport path, along which the plastic parisons are transported in the reshaping stations, and separates this transport path (hermetically) from an unsterile environment.

Furthermore, according to the embodiments of the invention the arrangement has a changing robot which is suitable and intended for demounting and/or mounting the blow molds on the blow mold supports associated therewith, as well as a magazine device which is suitable and intended for at least temporary storage of the blow molds.

In this case a sterile room is provided, in which at least one and precisely one blow mold set is stored or can be stored.

Furthermore, the embodiments of the present invention are directed to an arrangement for reshaping plastic parisons into plastic containers. This arrangement has a movable support on which a plurality of reshaping stations for reshaping plastic parisons into plastic containers are arranged, wherein these reshaping stations each have blow molds which are suitable and intended for shaping the plastic parisons, and which are arranged at least indirectly on blow mold supports.

Furthermore, the arrangement has a changing device and in particular a changing robot which is suitable and intended for mounting and/or demounting the blow molds, as well as a magazine device which is suitable and intended for at least temporary storage of the blow molds.

According to the embodiments of the invention the magazine device is suitable and intended for accommodating a plurality of sets of blow molds. Thus, as mentioned above, this is a dynamic magazine device and/or a dynamic store. In contrast to this only one blow mold set is stored in the above-mentioned magazine device.

Therefore, with regard to the machine it is also proposed that a magazine device is provided which is suitable and intended to accommodate a plurality of sets of blow molds, in order in this way to be able to carry out a change of blow mold more easily.

In this case a plurality of different sets of blow molds are selectable inside the magazine device and the access to these blow molds can be facilitated.

In a further preferred embodiment at least one magazine device is arranged inside a clean room. In this case it is possible both that a magazine device, which is suitable and intended only to accommodate a blow mold set, is arranged inside a clean room, as well as the above-mentioned dynamic magazine device, which is suitable and intended for accommodating a plurality of blow molds.

In a further preferred embodiment, it is also conceivable that a magazine device itself is designed to be aseptic, that is to say it is sterilized for example by means of sterilising agents.

In a further preferred method, the magazine device is suitable and intended to accommodate the blow mold or the blow molds when these blow molds are put together and/or in an assembled state. In this state for example the side parts can be fastened to one another and/or a base part can be fastened to the side parts, so that the blow mold can be removed in its entirety, that is to say in particular with side part and base parts.

In this case it is possible that the blow molds (comprising two mold shells and a base mold) are not actually assembled, but are held together by the magazine and/or the robot gripper as an assembly. In this case it is possible that the base mold is held by means of a centring ring in the two mold shells. The mold shells are preferably pressed together by robot grippers or held together in the magazine by this latter.

In a further advantageous embodiment, the magazine device has—in particular movable—receiving means for accommodating the blow molds. In this case it is conceivable and preferable that in each case a receiving means is suitable and intended for accommodating a blow mold. However, stationary receiving means could also be provided.

In a further advantageous embodiment, the magazine device has a selection device which enables an automatic selection of a blow mold set. Thus, for example in response to a user input a specific set of blow molds can be selected. It would also be possible that this selection device is coupled to a controller of the machine, and this controller determines which set of blow molds should be removed.

It is also proposed here that, in a blow molding machine, in particular a stretch blow molding machine and in particular an aseptic stretch blow molding machine with an automatic mold change, a store and in particular a dynamic store is connected to the machine. In this dynamic store a plurality of blow mold sets with blow molds can be stored as a mold set (a base mold with two side parts). In this case this dynamic store can be designed inter alia as a vertical or horizontal carousel rack such as for example a paternoster, a tower rack, a high-level rack, a mobile rack or the like.

Such a store contains a plurality of systems for blow mold storage, that is to say blow mold magazines. Thus, a plurality of blow mold sets can be stored in this store. As mentioned above, the blow molds are inserted as a mold set (that is to say, consisting of at least one base mold and two side parts) into the blow mold storage.

In this case these storage systems in this dynamic store can be arranged movably in the store or can be moved by a shelf operating device or the like in a dynamic store or can be retrieved therefrom. A required blow mold set can be selected in the dynamic store by an automatic signal from a robot or by the machine or also selection of an operator.

In a preferred method the dynamic store moves the storage systems in such a way that the storage system is provided with a required blow mold set for a mold change.

In a preferred method the arrangement of a dynamic store takes place directly on the region of the automatic mold change and in particular with an interface thereto. In a further preferred method, the protection region of the robot cell is connected to that of a store.

Furthermore, it is possible, as mentioned above, that this store or the magazine device is not sterilisable or is also sterilisable with sterilising media such as $H_2O_2$, and/or can be designed to be aseptic.

Furthermore, it is possible that the storage system for the mold sets or the blow molds is not sterilisable or is sterilisable with hydrogen peroxide or also is designed to be aseptic. In particular, if the magazine device or the storage system is a sterilisable and/or aseptic storage system, this storage system and also the robot cell is designed in such a way that an internal pressure can be applied to it which is greater than its ambient pressure.

In a further preferred method, the storage device or the magazine is coupled for control purposes by the control device to a type selection of the blow molding machine or to a complete line and automatically provides the blow molds appropriate for the change of type.

Different procedures can be selected for storing the blow molds inside the store. Thus, it would be possible that the molds are stored in a magazine, which can take place in the same or similar manner to the procedure in the case of a mold change robot. In addition, it would also be possible that these magazines in turn are stored in a store.

In addition, it would also be possible to store the blow molds directly in a store.

In a preferred embodiment the storage system at least one, two interface(s) or bulkheads. In this case an interface to the outside can be provided in order to fill the storage system or the store and/or in order to insert the individual storage systems. By means of this interface the store or the magazine device can be loaded and unloaded without interruption of production by the machine or plant. In addition, an optional bulkhead can be provided for separation between a possible sterile dynamic store and the environment. A further interface to the machine and/or to the mold change region of the machine can be provided.

In addition, an optional bulkhead to a sterile room can also be provided.

This embodiment of the invention makes it possible to store blow molds directly on the blow molding machine and also enables an even faster mold change by omitting the setting up of a blow mold magazine (transport paths from the store to the machine) and changing of the blow mold magazine is not needed. In this case a blow mold can be carried out on the machine fully automatically and entirely without an operator. Also, preparations by the operator can be omitted.

In addition, the danger of damage and ingress of dirt during transport and an external storage can also be eliminated.

Furthermore, it is possible that the above-mentioned sterile room or clean room surrounds the entire arrangement. However, it would also be possible that the sterile room only surrounds the transport path along which the reshaping stations are transported during the working process.

This sterile room has at least two walls which delimit this sterile room relative to the environment, wherein particularly these walls are movable with respect to one another. Thus, for example sealing systems, such as so-called channel seals or water locks, can be used for sealing of the sterile room.

The reshaping stations have supports which are pivotable with respect to one another and on which the side parts of the blow molds are arranged. In a further preferred embodiment, the blow molds also have a base part which is particularly arranged on a base part support.

The blow molds can be removed in an assembled state from their supports.

In a further advantageous embodiment, the arrangement has at least one sterilising device which is suitable and intended for applying an in particular flowable sterilising medium to components of the arrangement and/or the blow molds.

In a further preferred embodiment, the changing robot is likewise arranged in a clean room. This clean room can be a stationary clean room.

This clean room in which the changing robot is located is or can be segregated with the aid of a bulkhead or an air lock relative to the clean room in which the plastic parisons are reshaped into the plastic containers. This means that the changing robot can be separated from the actual blow molding machine in particular during operation of the blow molding machine.

In a further preferred embodiment at least one magazine device is also arranged inside a clean room. As mentioned above, this clean room can be the same clean room in which the changing robot is also arranged. However, it would also be possible that the magazine device for storing the blow molds is arranged in a further clean room, which then can be segregated by means of a further air lock and/or a further bulkhead relative to the clean room in which the changing robot is arranged.

In a further advantageous embodiment, the arrangement has at least one checking unit, which is suitable for checking at least one physical characteristic of the blow molds or a characteristic which relates to an arrangement of the blow molds on the blow mold supports. Thus, for example the checking device can check whether a correct blow mold is arranged on its support and/or whether the blow mold is correctly positioned or mounted on its blow mold support.

Setup times and also machine shutdown times can be reduced by the procedure or the arrangement described here. At the same time errors by the operator in the case of a change of blow mold can be precluded by carrying out an automatic mold change.

Due to the possibility of sterilising the blow molding wheel without the blow molds and sterilising the blow molds separated into a base mold and the side parts outside the blow molding wheel, it is also possible that spaces at the rear of blow molds (mold shell and mold base) and also the corresponding counterpart faces on the mold support are sterilized. In addition, no operator intervention takes place in the sterile region of the blow molding wheel during the mold change. Thus, no contamination can enter this region.

In addition, there is also no operator needed in the event of a mold change bound and during this time the operator can undertake other functions such as for example changing handling parts, changing labels and the like.

A preferred method for automatic change of blow molds is described below. In this case it is possible that an operator equips the blow mold magazine with the blow molds to be used and/or also provides an empty blow mold magazine via a bulkhead. An air lock or a bulkhead to the clean room of the plant remains closed. In this way the entire machine remains sterile and the production can continue during the set-up process.

Before the sterilization of the blow mold a changing robot and/or the above-mentioned checking device can carry out a check of correctness and correct seating of the blow molds. This can take place for example by means of RFID tags and/or a mechanical intervention in the blow molds.

At this stage in the event of problems (for example use of an incorrect mold, a correctly or incorrectly identified mold and the like) the operator can still intervene before the blow molds are sterilized. For the purpose of sterilization it is possible that two bulkheads or air locks are closed while a bulkhead which connects the magazine device to the changing robot is open. In this case the machine or the blow molding wheel also remains sterile and checking by the changing robot is also possible during production.

After successful checking of the blow mold a change of blow mold can be started. For this purpose, it is possible to close a bulkhead relative to the environment and on the other hand to open the bulkhead to the machine. The changing robot first of all takes all blow molds out of the mold supports. Subsequently the blow molding machine is sterilized without blow molds, so that the spaces at the rear of mold shells and base molds are disinfected.

At the same time a sterilization of an extended sterile room with a mold change robot can take place and also a sterilization of the extended sterile room with the blow mold magazine and the blow molds can also take place.

After the sterilization the new blow molds are inserted by the changing robot into the mold support. The bulkhead, which constitutes a connection to the space occupied by the changing robot, is closed again and the production can be resumed again.

In a further embodiment a dynamic store in which a plurality of blow mold sets are stored in blow mold magazines can also be connected to the extended sterile room in which the changing robot is located. If the operator selects a new blow mold, or if a signal comes from the changing robot or the control of the machine, it is possible that this dynamic store moves the blow mold magazines accordingly.

In this case a bulkhead can open, and the blow mold magazine with the required blow mold set and, in the case of a sterilization of the machine without molds, also an empty blow mold magazine are provided.

In a further preferred embodiment, the changing robot is also suitable and intended for checking correct seating of the individual blow molds and in particular checking this correct seating the blow molds already inside a magazine device. In addition, the changing robot is suitable and intended for checking or for ensuring which blow mold is arranged at which position inside the magazine device. This can take place for example by reading RFID elements. In addition, it is also possible to check whether the respective blow mold belongs to the correct mold set. In addition, it is also conceivable that a changing robot is suitable and intended to arrange the blow molds on blow mold supports respectively intended for them.

In this way such a dynamic store or such a dynamic magazine device is particularly also separated (in particular hermetically) from the environment by means of a further bulkhead. In addition, it would also be possible that the dynamic store is regarded as a further sterile room which is also designed to be sterilisable by means of a sterilising agent such as for example H2O2. In this case a bulkhead can also be omitted, or the sterile room of this dynamic store and the sterile room of the robot device can be designed as a sterile room.

BRIEF DESCRIPTION

Figure 2:
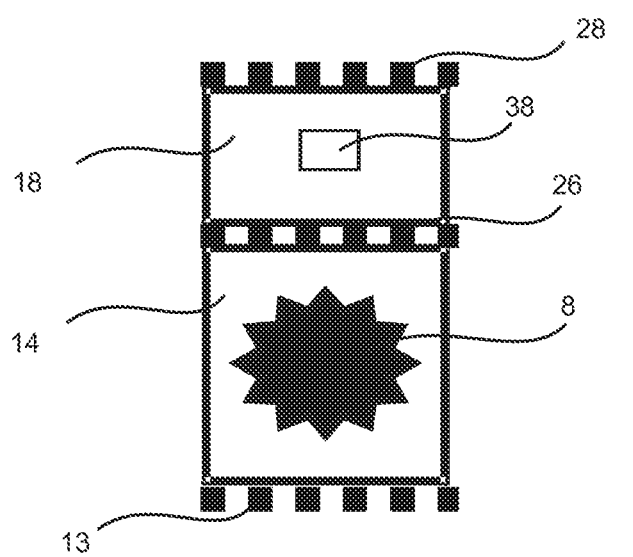

Some of the embodiments will be described in detail, with reference to the following figures, wherein like designations denote like members, wherein:

FIG. 1 shows a schematic representation of a plant for producing plastic containers; and FIG. 2 shows a detail of the airlock portion of the plant shown in FIG. 1.

DETAILED DESCRIPTION

FIG. 1 shows an arrangement 50 for producing plastic containers. This arrangement 50 has a heating device 4, such as for example an oven, inside which the plastic parisons are heated. In this case this oven can have a revolving transport chain (not shown) on which a plurality of holding devices for holding the plastic parisons are arranged. In addition, this heating device 4 can also have heating elements (not shown), past which the plastic parisons are guided.

The heating device 4 is adjoined by a (transport and) sterilization module 6, which is suitable and intended for sterilising the heated plastic parisons. In this case this transport and sterilization module 6 can for example have a sterilising device 62, which likewise transports the plastic parisons and carries out a sterilization of the plastic parisons during this transport. In this case for example beam fingers, which sterilise the inner walls of the plastic parisons by means of electron beams, can penetrate into the plastic parisons. In addition, sterilization by means of a flowable medium, such as for example hydrogen peroxide, can also take place. The reference 64 designates a further transport device, which transfers the in this way sterilized plastic parisons to a reshaping device 1 for reshaping the plastic parisons into plastic containers. The reference 66 identifies schematically a clean room which at least surrounds the transport path of the plastic parisons during sterilization thereof.

The reshaping device 1 has a rotatable support 2 on which a plurality of transforming stations 20 are arranged. In this case each of these reshaping stations has side part supports 22 which are pivotable with respect to one another and blow molds 10 arranged on these side part supports.

The reference 12 designates quite schematically a clean room, inside which the reshaping stations 20 are transported and/or inside which the plastic parisons are reshaped into plastic containers. In this case this clean room 12 can be designed in such a way that it surrounds the transport path of the reshaping stations like a channel.

The reference 8 designates a robot device which serves for changing the blow molds of the reshaping stations. In this case this changing device or this changing robot 8 is arranged inside a second clean room 14. This second clean room 14 can be connected by means of an air lock device 13 or a bulkhead to the clean room 12 of the machine 1, or this connection can be interrupted. Thus, it is possible that the clean room 14, in which the changing robot 8 is located in a normal operating mode, is separated from the clean room 12, in which the reshaping process with the reshaping stations 20 proceeds.

The reference 16 relates to a third clean room in which a mold magazine 36 is arranged which is only shown schematically. By means of a further bulkhead 24 or a further air lock this third clean room 16 can be separated from the clean room 14 in which the changing robot 8 is located. Two or more mold magazines could also be accommodated in the third clean room.

Within the context of a changing operation the changing robot 8 can remove blow molds from the magazine 36 or can place blow molds originating from the reshaping device in this mold magazine.

Due to this configuration it is possible that a set-up process can be ended already in the normal operating mode of the blow molding machine. Thus, it is possible that the bulkhead or the air lock 24 is also closed, and in this way the clean rooms 16 and 14 are separated from one another.

The reference 18 designates a further optional clean room, in which a dynamic magazine 38 can be arranged. In this case this dynamic magazine 38 is suitable and intended for accommodating a plurality of sets of blow molds. In this case this magazine can be present in particular instead of the magazine 36. A further air lock device 26 or a bulkhead can separate the clean room 18 from the clean room 16. In this way it is also possible that in the event of a change of blow mold an operation of the machine itself can be continued.

The reference 28 designates a further bulkhead or an air lock which serves for segregation of the clean room 18 relative to the (unsterile) environment.

FIG. 2 shows a further embodiment of the present invention. In this embodiment the clean room 18 in which the dynamic mold magazine 38 is located is arranged directly on the clean room 14 in which the changing robot 8 is located. In this case this mold magazine is suitable for accommodating a plurality of sets of blow molds. By means of a controller it is possible that the robot removes required blow molds in a targeted manner from the dynamic magazine 38. Again, the air lock device or the bulkhead 26 is shown which separates the clean rooms 14 and 18 from one another. The individual illustrated clean rooms 14, 16 and 18 are also sterilisable separately, and the individual magazines 36 and 38 are also sterilizable. In addition, the changing robot itself or the components thereof is also sterilizable. It would also be possible that a protective cover which shields the robot is provided.

The applicant reserves the right to claim all the features disclosed in the application documents as essential to the embodiments of the invention in so far as they are individually or in combination novel over the known art. Furthermore, it is pointed out that features which may be advantageous per se have also been described in the individual drawings. The person skilled in the art recognises immediately that a specific feature described in a drawing may also be advantageous without the incorporation of further features from this drawing. Furthermore, the person skilled in the art recognises that advantages may also result from a combination of several features shown in individual drawings or in different drawings.

Although the invention has been illustrated and described in greater detail with reference to the preferred exemplary embodiment, the invention is not limited to the examples disclosed, and further variations can be inferred by a person skilled in the art, without departing from the scope of protection of the invention.

For the sake of clarity, it is to be understood that the use of "a" or "an" throughout this application does not exclude a plurality, and "comprising" does not exclude other steps or elements.

LIST OF REFERENCES 1 reshaping device
2 support
4 heating device
6 transport and sterilization device
8 changing robot
10 blow mold
12 clean room
13 air lock or bulkhead between machine 1 and clean room 14
14 clean room of the changing robot
16 clean room of the magazine device 36
18 clean room of the optional magazine device 38
20 reshaping station
22 blow mold support
24 air lock or bulkhead between the clean rooms 14 and 16
26 air lock or bulkhead between the clean rooms 16 and 18
28 air lock or bulkhead relative to the environment
36 magazine device
38 magazine device
50 arrangement
62 sterilizing device
64 further transport device
66 clean room

The invention claimed is:

1. A method for operating a machine for reshaping plastic parisons into plastic containers, wherein the machine has a movable support, on which a plurality of reshaping stations are arranged for reshaping plastic parisons into plastic containers, and these reshaping stations each have blow molds which are suitable and intended for shaping the plastic parisons and which are arranged at least indirectly on blow mold supports, wherein the blow molds are at least temporarily stored in a magazine device, wherein this magazine device is suitable and intended for accommodating a plurality of sets of blow molds, wherein the magazine device is a dynamic store which is constructed as a vertical or horizontal carousel rack and the arrangement of the dynamic store takes place directly in a region of the mold change, wherein a changing device is arranged in a first clean room, the changing device can be separated by a first air lock device or bulkhead from the machine for reshaping the plastic parisons, and the magazine device is arranged in a second clean room, which can be segregated by means of a second airlock or bulkhead relative to the first clean room in which the changing device is arranged.

2. The method according to claim 1, wherein the blow molds are removed from the blow mold supports by the changing device.

3. The method according to claim 1, wherein a respective blow mold set is configured to be selected by at least one of the changing device, an operator via a control device, and a controller of the blow molding machine.

4. The method according to claim 1, wherein at a predetermined time the magazine device provides a respectively required mold set.

5. The method according to claim 1, wherein the blow molds removed from the blow mold supports are stored at least temporarily in the magazine device.

6. The method according to claim 1, wherein the removed blow molds are sterilized at least one of before and during the storage in the magazine device.

7. An arrangement for reshaping plastic parisons into plastic containers with a movable support on which a plurality of reshaping stations are arranged for reshaping plastic parisons into plastic containers, and these reshaping stations each have blow molds which are suitable and intended for shaping the plastic parisons and which are arranged at least indirectly on blow mold supports, wherein, furthermore, the arrangement has a changing device which is suitable and intended for demounting and/or mounting the blow molds, as well as a magazine device which is suitable and intended for at least temporary storage of the blow molds, wherein the magazine device is suitable and intended for accommodating a plurality of sets of blow molds, wherein the magazine device is a dynamic store which is constructed as a vertical or horizontal carousel rack and the arrangement of the dynamic store takes place directly in a region of the mold change, wherein the changing device is arranged in a clean room, the changing device can be separated by an air lock device or a bulkhead from the machine for reshaping the plastic parisons, and the magazine device is arranged in a further clean room, which is segregated by means of an airlock or a bulkhead relative to the clean room in which the changing device is arranged.

8. The arrangement according to claim 7, wherein the magazine device is suitable and intended for accommodating the blow molds in an assembled state of these blow molds.

9. The arrangement according to claim 7, wherein the magazine device has movable receiving means suitable and intended for accommodating the blow molds.

10. The arrangement according to claim 7, wherein the magazine device is coupled to a control device of the blow molding machine in such a way that an automatic selection of a blow mold set is made possible.

11. The arrangement according to claim 9, wherein the arrangement has at least one sterilising device in order to apply a flowable sterilising medium to components of the arrangement and/or the blow molds.

12. The arrangement according to claim 7, wherein the magazine device is movable in its entirety relative to the arrangement.

13. The arrangement according to claim 7, wherein the magazine device is designed to be aseptic.

14. The method according to claim 1, wherein the changing device is enabled to prepare a change of blow mold in the magazine during production of the plastic containers by the machine.

15. The method according to claim 1, wherein the magazine device is coupled for control purposes by a control device to a type selection of the machine, and automatically provides blow molds appropriate for a change of type.

16. The method according to claim 1, wherein the changing device is suitable and intended for checking correct seating of the blow molds.

17. The method according to claim 1, wherein the changing device is suitable and intended for checking or for insuring which blow mold is arranged in which position inside the magazine device by reading RFID elements.

18. The method of claim 1, further wherein the machine for reshaping the plastic parisons is arranged in a third clean room, such that the changing device can be separated by the first air lock device or bulkhead from the third clean room.

* * * * *